US010815292B2

(12) United States Patent
Nieznański et al.

(10) Patent No.: US 10,815,292 B2
(45) Date of Patent: Oct. 27, 2020

(54) PRION PROTEIN-DENDRIMER CONJUGATES FOR USE IN TREATMENT OF ALZHEIMER DISEASE

(71) Applicants: Instytut Biologii Doświadczalnej im. Marcelego Nenckiego Polskiej Akademii Nauk, Warsaw (PL); Case Western Reserve University, Cleveland, OH (US)

(72) Inventors: Krzysztof Nieznański, Warsaw (PL); Hanna Nieznańska, Warsaw (PL); Witold K. Surewicz, Moreland Hills, OH (US); Krystyna Surewicz, Moreland Hills, OH (US); Magdalena Bandyszewska, Gliwice (PL)

(73) Assignees: Instytut Biologii Doświadczalnej im. Marcelego Nenckiego Polskiej Akademii Nauk, Warsaw (PL); Case Western Reserve University, Cleveland, OH (US)

( * ) Notice: Subject to any disclaimer, the term of this patent is extended or adjusted under 35 U.S.C. 154(b) by 0 days.

(21) Appl. No.: 16/300,214

(22) PCT Filed: May 10, 2017

(86) PCT No.: PCT/IB2017/052733
§ 371 (c)(1),
(2) Date: Nov. 9, 2018

(87) PCT Pub. No.: WO2017/195131
PCT Pub. Date: Nov. 16, 2017

(65) Prior Publication Data
US 2019/0092837 A1    Mar. 28, 2019

(30) Foreign Application Priority Data
May 11, 2016    (PL) .......................................... 417159

(51) Int. Cl.
| C07K 14/705 | (2006.01) |
| A61P 25/28 | (2006.01) |
| A61K 47/59 | (2017.01) |
| C07K 14/47 | (2006.01) |
| A61K 38/17 | (2006.01) |
| A61K 47/60 | (2017.01) |

(52) U.S. Cl.
CPC ........ *C07K 14/70596* (2013.01); *A61K 38/17* (2013.01); *A61K 38/177* (2013.01); *A61K 38/1709* (2013.01); *A61K 47/595* (2017.08); *A61K 47/60* (2017.08); *A61P 25/28* (2018.01); *C07K 14/47* (2013.01); *C07K 2319/00* (2013.01)

(58) Field of Classification Search
None
See application file for complete search history.

(56) References Cited

FOREIGN PATENT DOCUMENTS

| WO | 02/42462 | | 5/2002 | |
| WO | WO 2005/095633 | * | 10/2005 | |
| WO | WO 2008/134034 | * | 11/2008 | ............. C07K 16/00 |
| WO | 2009/041902 | | 4/2009 | |
| WO | WO 2009/041902 | * | 4/2009 | ............. G01N 33/68 |
| WO | WO 2014/026283 | * | 2/2014 | ............. C07K 14/81 |

OTHER PUBLICATIONS

Löfgren et al., FASEB J. 22, 2177-2184 (2008) (Year: 2008).*
Ren et al., Biomaterials 33 (2012) 3324-3333 (Year: 2012).*
Nienanska et al., BBA—Molecular Basis of Disease, 2018; 1864: 2143-2153 (Year: 2018).*
International Search Report and Written Opinion of the International Searching Authority, dated Aug. 3, 2017 in corresponding International Patent Application No. PCT/IB2017/052733.
Lofgren et al., "Antiprion properties of prion protein-derived cell-penetrating peptides", The FASEB Journal, vol. 22, No. 7: 2177-2184 (2017).

* cited by examiner

*Primary Examiner* — Christina M Borgeest
(74) *Attorney, Agent, or Firm* — Wenderoth, Lind & Ponack, L.L.P.

(57) ABSTRACT

The present invention relates to PrP-derived peptide fragments with SEQ ID NO: 1 or SEQ ID NO: 2 or SEQ ID NO: 3 or SEQ ID NO: 4 for use as a medicament in the treatment of Aβ amyloidogenesis-related pathologies and/or Aβ-related toxicity, in particular of Alzheimer disease (AD), to a conjugate comprising PrP-derived peptide fragments with SEQ ID NO: 1 or SEQ ID NO: 3 and/or SEQ ID NO: 2 or SEQ ID NO: 4 and a carrier molecule, wherein the carrier molecule is a pharmacologically admissible molecule, preferably a low-generation dendrimer such as PAMAM dendrimer, and a method of manufacturing the above conjugate.

Figure 1:
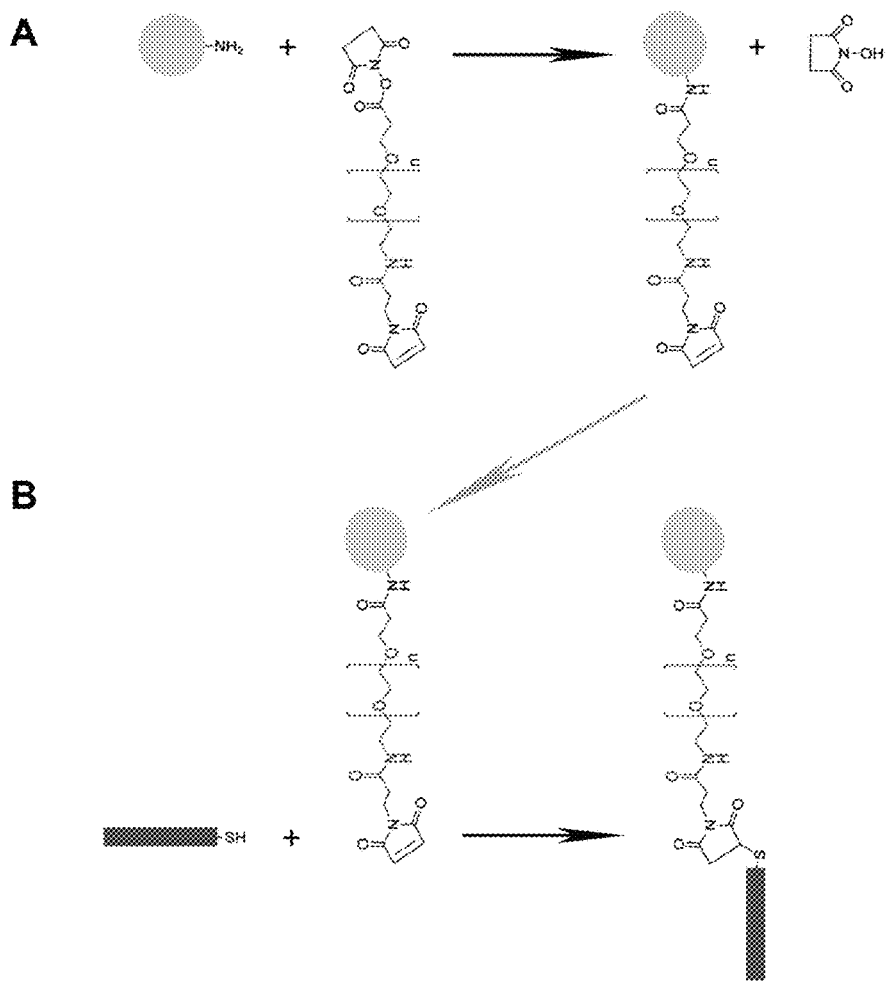

18 Claims, 3 Drawing Sheets
Specification includes a Sequence Listing.

- PAMAM dendrimers; single primary amino group is shown for simplicity
- Synthetic peptides: fragments of PrP and BBB-penetrating peptide
- MAL-PEG-NHS; n represents the number of ethylene glycol units

PRION PROTEIN-DENDRIMER CONJUGATES FOR USE IN TREATMENT OF ALZHEIMER DISEASE

The present invention relates to conjugates of prion protein with dendrimers as inhibitors of Aβ peptide amyloidogenesis and cytotoxicity of potential application in Alzheimer disease therapy.

Alzheimer disease (AD) is the most frequent amyloidosis characterized by extracellular accumulation of senile plaques in the brain (Selkoe D J (2001) *Physiol. Rev.* 81, 741-766; Selkoe D J (2002) *Science* 298, 789-791). The plaques are composed of amyloid-β (Aβ) peptides. Aβ peptides are generated from membrane-bound amyloid precursor protein (APP) by proteolytic cleavage catalyzed by β- and γ-secretases. These peptides, consisting of 37-43 amino acid residues, have high propensity to form fibrillar aggregates-amyloids. In general, longer peptides are less soluble and more amyloidogenic (Jarrett J T, Berger E P, Lansbury P T Jr. (1993) *Ann. N Y Acad. Sci.* 695, 144-8). The major component of the senile plaques in AD is Aβ1-42, and increase in the Aβ1-42/Aβ1-40 ratio or rise of the levels of Aβ1-42 or Aβ1-43 predispose to AD (Welander H, Frånberg J, Graff C, Sundström E, Winblad B, Tjernberg L O (2009) *J. Neurochem.* 110, 697-706; Kuperstein I, Broersen K, Benilova I, Rozenski J, Jonckheere W, Debulpaep M, Vandersteen A, Segers-Nolten I, Van Der Werf K, Subramaniam V, Braeken D, Callewaert G, Bartic C, D'Hooge R, Martins I C, Rousseau F, Schymkowitz J, De Strooper B (2010) *EMBO J.* 29, 3408-20). Aβ peptides composed of 37-40 residues are presumed comparatively benign. In familial form of the disease (fAD) elevated production of aggregation-prone Aβ peptides correlates with point mutations influencing proteolytic processing of APP (Scheuner D, Eckman C, Jensen M, Song X, Citron M, Suzuki N, Bird T D, Hardy J, Hutton M, Kukull W, Larson E, Levy-Lahad E, Viitanen M, Peskind E, Poorkaj P, Schellenberg G, Tanzi R, Wasco W, Lannfelt L, Selkoe D, Younkin S (1996) *Nat. Med.* 2, 864-70). For many years, neurotoxic activity has been attributed mainly to fibrillar aggregates of Aβ. However, more recent studies have demonstrated that nonfibrillar aggregates, referred to as soluble oligomers, are more cytotoxic than Aβ amyloid fibrils. Aβ oligomers were shown to act as potent neurotoxins in vitro and in vivo (Small D H, Mok S S, Bornstein J C (2001) *Nat. Rev. Neuroscience* 2, 595-598; Walsh D M, Selkoe D J (2007) *J. Neurochem.* 101, 1172-1184; Roychaudhuri R, Yang M, Hoshi M M, Teplow D B (2009) *J. Biol. Chem.* 284, 4749-4753) and their presence correlates well with the disease progression in AD patients and animal models of the disease (Walsh D M, Selkoe D J (2007) *J. Neurochem.* 101, 1172-1184; Klein W L, Krafft G A, Finch C E (2001) *Trends Neurosci.* 24, 219-224; Haass C, Selkoe D J (2007) *Nat. Rev. Molecular Cell Biology* 8, 101-112). Despite decades of research on AD no effective therapy has been proposed to date. Among promising approaches were beta-sheet breaking peptides, compounds inhibiting amyloidogenesis and monoclonal antibodies raised against oligomers of Aβ peptides (Selkoe D J (2002) *Science* 298, 789-791; Soto C, Kindy M S, Baumann M, Frangione B (1996) *Biochem. Biophys. Res. Commun.* 226, 672-680; Gandy S, DeKosky S T (2013) *Annu. Rev. Med.* 64, 367-83). In light of antiamyloidogenic activity, synthetic nanoparticles called dendrimers have been evaluated as a potential drug in AD (Klajnert B, Cladera J, Bryszewska M (2006) *Biomacromolecules* 7, 2186-91; Klajnert B, Cortijo-Arellano M, Cladera J, Bryszewska M (2006) *Biochem. Biophys. Res. Commun.* 345, 21-8; Klajnert B, Cangiotti M, Calici S, Majoral J P, Caminade A M, Cladera J, Bryszewska M, Ottaviani M F (2007) *Macromol. Biosci.* 7, 1065-74; Wasiak T, Ionov M, Nieznanski K, Nieznanska H, Klementieva O, Granell M, Cladera J, Majoral J P, Caminade A M, Klajnert B (2012) *Mol. Pharm.* 9, 458-69). Dendrimers are tree-like branched polymers of spherical geometry. They are composed of dendrons radiating from a central core, where each layer of branching units constitutes so-called generation (G). Consistently, dendrimer's molecular weight, size and number of surface groups increases with generation number. Owing to their high aqueous solubility, compact structure and large number of surface groups accessible to functionalization dendrimers have been commonly considered ideal carriers of therapeutic molecules, nucleic acids and contrast agents. Furthermore, it has been demonstrated that dendrimers bearing cationic functional groups directly affect in vitro amyloidogenesis of Aβ peptides. At particular dendrimer to peptide ratios, polypropylenimine (PPI) dendrimers increased rate of fibrillization of Aβ1-28, phosphorus dendrimers reduced the rate, whereas polyamidoamine (PAMAM) dendrimers completely inhibited the process (Klajnert B, Cladera J, Bryszewska M (2006) *Biomacromolecules* 7, 2186-91; Klajnert B, Cortijo-Arellano M, Cladera J, Bryszewska M (2006) *Biochem. Biophys. Res. Commun.* 345, 21-8; Klajnert B, Cangiotti M, Calici S, Majoral J P, Caminade A M, Cladera J, Bryszewska M, Ottaviani M F (2007) *Macromol. Biosci.* 7, 1065-74; Wasiak T, Ionov M, Nieznanski K, Nieznanska H, Klementieva O, Granell M, Cladera J, Majoral J P, Caminade A M, Klajnert B (2012) *Mol. Pharm.* 9, 458-69). Effects of dendrimers are generation dependent and correlate with the number of cationic groups. Unfortunately, the most effective cationic PAMAM dendrimers appear to be unspecific and cytotoxic (Jain K, Kesharwani P, Gupta U, Jain N K (2010) *Int. J. Pharm.* 394, 122-142; Sadekar S, Ghandehari H (2012) *Adv. Drug. Deliv. Rev.* 64, 571-88). Full generation PAMAM dendrimers with ethylene diamine core and amidoamine branching structure bear primary amine groups on their surface. Their effectiveness as well as cytotoxicity increases with the number of amino groups. This toxicity is believed to be related to electrostatic interactions with negative charges on the cell membrane and other molecules of important physiological functions. Thus, the new approach is to reduce cytotoxicity and increase specificity of dendrimers by modification/functionalization of the surface groups. Binding to Aβ1-42 oligomers and rescue of synaptic plasticity in ex vivo experiments have been demonstrated for conjugates of PAMAM dendrimers with unnatural biomimetic polymers—foldamers (Fülöp L, Mándity I M, Juhász G, Szegedi V, Hetényi A, Wéber E, Bozsó Z, Simon D, Benkő M, Király Z, Martinek T A (2012) *PLoS One* 7, e39485). Direct binding to PrP has been shown for Aβ1-42 in a form of soluble oligomers and amyloid fibrils (Lauren J, Gimbel D A, Nygaard H B, Gilbert J W, Strittmatter S M (2009) *Nature* 457, 1128-132; Balducci C, Beeg M, Stravalaci M, Bastone A, Sclip A, Biasini E, Tapella L, Colombo L, Manzoni C, Borsello T, Chiesa R, Gobbi M, Salmona M, Forloni G (2010) *Proc. Natl. Acad. Sci. USA* 107, 2295-2300; Chen S, Yadav S P, Surewicz W K (2010) *J. Biol. Chem.* 285, 26377-26383; Williams T L, Choi J K, Surewicz K, Surewicz W K (2015) *ACS Chem. Neurosci.* 6, 1972-80; Nieznanski K, Surewicz K, Chen S, Nieznanska H, Surewicz W K (2014) *ACS Chem. Neurosci.* 5, 340-5). The interaction with highly neurotoxic form of Aβ peptide has opened promising field in AD studies. The major binding sites for Aβ1-42 have been mapped within residues 23-27 and 95-110, both encompassing basic clusters of the N-terminal flexible domain of PrP (Lauren J, Gimbel D A, Nygaard H B, Gilbert J W, Strittmatter S M (2009) *Nature* 457, 1128-132; Chen S, Yadav S P, Surewicz W K (2010) *J. Biol. Chem.* 285, 26377-26383; Fluharty B R, Biasini E, Stravalaci M, Sclip A, Diomede L, Balducci C, La Vitola P, Messa M, Colombo L, Forloni G, Borsello T, Gobbi M, Harris D A (2013) *J. Biol. Chem.* 288, 7857-66). The binding of the basic clusters is also influenced by the length of the linking sequence between them (Fluharty B R, Biasini E, Stravalaci M, Sclip A, Diomede L, Balducci C, La Vitola P, Messa M, Colombo L, Forloni G, Borsello T, Gobbi M, Harris D A (2013) *J. Biol. Chem.* 288, 7857-66). PrP and its proteolytic fragment encompassing residues 23-110/111 (called N1) bind to Aβ oligomers with nanomolar affinity (Balducci C, Beeg M, Stravalaci M, Bastone A, Sclip A, Biasini E, Tapella L, Colombo L, Manzoni C, Borsello T, Chiesa R, Gobbi M, Salmona M, Forloni G (2010) *Proc. Natl. Acad. Sci. USA* 107, 2295-2300; Fluharty B R, Biasini E, Stravalaci M, Sclip A, Diomede L, Balducci C, La Vitola P, Messa M, Colombo L, Forloni G, Borsello T, Gobbi M, Harris D A (2013) *J. Biol. Chem.* 288, 7857-66). Importantly, secreted PrP and N1 have been shown to protect neurons against cytotoxic Aβ oligomers (Calella A M, Farinelli M, Nuvolone M, Mirante O, Moos R, Falsig J, Mansuy I M, Aguzzi A (2010) *EMBO Mol. Med.* 2, 306-314; Guillot-Sestier M V, Sunyach C, Ferreira S T, Marzolo M P, Bauer C, Thevenet A, Checler F (2012) *J. Biol. Chem.* 287, 5021-5032). While this effect has been proposed to be mediated by modulation of the p53 pathway our studies provided explanation related to a direct interaction between PrP and early misfolded species of Aβ (Nieznanski K, Choi J K, Chen S, Surewicz K, Surewicz W K (2012) *J. Biol. Chem.* 287, 33104-33108). We have demonstrated that PrP and its N-terminal fragments act as potent inhibitors of Aβ1-42 amyloidogenesis in vitro shifting aggregation pathway towards nontoxic Aβ assemblies (Nieznanski K, Choi J K, Chen S, Surewicz K, Surewicz W K (2012) *J. Biol. Chem.* 287, 33104-33108). Importantly, PrP reduced cytotoxicity of Aβ oligomers in the cells of neuronal origin, even at very low molar ratios. Subsequently, neutralization of neurotoxic Aβ oligomers by N1 fragment of PrP has been confirmed by other laboratories (Fluharty B R, Biasini E, Stravalaci M, Sclip A, Diomede L, Balducci C, La Vitola P, Messa M, Colombo L, Forloni G, Borsello T, Gobbi M, Harris D A (2013) *J. Biol. Chem.* 288, 7857-66; Béland M, Bédard M, Tremblay G, Lavigne P, Roucou X (2014) *Neurobiol. Aging.* 35, 1537-48). It has been demonstrated that N1 inhibits toxicity of Aβ peptide in the culture of hippocampal neurons and suppresses Aβ-induced memory impairment in a mouse model. Recently, it has been also shown that PrP and N1 reduce Aβ oligomers-induced inhibition of long-term potentiation (LTP), an important marker of synaptic plasticity defects associated with AD (Scott-McKean J J, Surewicz K, Choi J K, Ruffin V A, Salameh A I, Nieznanski K, Costa A C, Surewicz W K (2016) *Neurobiol. Dis.* 91, 124-31). These observations offer new ways for pharmacological intervention in AD by using analogues/derivatives of PrP or its fragments.

Therefore, a solution according to the present invention will exhibit the anti-β properties of the N1 fragment of PrP and it will retain a high specificity for toxic Aβ species, will not exhibit the undesirable properties of N1, namely in that it will not form oligomers, will further demonstrate no systemic toxicity, and will not have immunogenicity, will furthermore readily penetrate the brain-blood barrier (BBB), will exhibit high biostability, and will mainly consist of pharmaceutically admissible components.

The above stated problems have been solved by the present invention.

The prion protein (PrP) and its fragments, in their form unbound to the cell membrane, play a neuroprotective role against toxic oligomers of Aβ1-42 peptide—a species responsible for the pathogenesis of Alzheimer disease (AD). Numerous studies have demonstrated that PrP and its N-terminal fragment bind oligomers as well as amyloid fibrils of Aβ peptide, inhibit amyloidogenesis of Aβ, and reduce Aβ synaptotoxicity and cytotoxicity. These observations suggest that PrP, its fragments and derivatives thereof may be useful for the design of therapeutics inhibiting progression of Alzheimer disease. However, PrP may undergo oligomerization/aggregation as well as proteolysis, and hence may have a short pharmacological half-life in organism. Additionally, intravenously administrated PrP is not able to cross the blood-brain barrier (BBB). Consequently, it can be difficult to achieve therapeutically significant brain levels of the protein in patients. Furthermore, full-length PrP has been demonstrated to have multiple interactions (beside that with Aβ peptide) and may influence numerous cellular processes.

To overcome above problems it is necessary to identify the shortest PrP fragment capable of inhibiting neurotoxicity of Aβ peptide and obtain bio-stable PrP derivatives that can be targeted to the brain. In the present invention, the PrP fragments retaining neuroprotective features against toxic Aβ peptide and the peptide allowing crossing of BBB are covalently bound to dendrimers—spherical polymers employed as drug vectors. The peptides are cross-linked directly to the reactive groups of dendrimer or indirectly via bi-functional PEG. Introduction of the flexible PEG linker allows adopting various mutual positions of the attached peptides, which may be important for the interaction with Aβ peptide, thus increasing efficacy of the conjugate of the present invention. Furthermore, the conjugates with dendrimers may render stability to PrP fragments (eg. prevent aggregation of PrP), ensure specific localization (targeting to the brain), and extend half-life in organism (decreased proteolytic degradation and reduced kidney excretion). Employment of the shortest effective PrP fragments (synthetic peptides) increases specificity of the conjugates and reduces costs of the synthesis.

Dendrimers are commercially available and frequently used as carriers of peptidic/proteinaceous drugs (numerous patents e.g. US patent application 5714166 A). Similarly, bi-functional derivatives of PEG are commercially available and commonly used for modification of these kinds of drugs (numerous patent applications e.g. EP0903152 A2; US20040115165 A1). Furthermore, BBB-penetrating peptides—natural ligands of low density lipoprotein receptor-related protein (LRP), such as Angiopep, are employed for delivery of drugs to the brain. Angiopep, which derives from human Kunitz domain, interacts with and undergoes transcytosis by LRP, a receptor expressed on the BBB (expressed on the brain capillary endothelial cells) (Demeule M, Currie J C, Bertrand Y, Ché C, Nguyen T, Régina A, Gabathuler R, Castaigne J P, Béliveau R (2008) *J. Neurochem.* 106, 1534-44). Importantly, LRP is overexpressed in A D and colocalizes with senile plaques (Rebeck G W, Reiter J S, Strickland D K, Hyman B T (1993) *Neuron* 11, 575-80). Conjugates of PAMAM dendrimers with Angiopep have been successfully used by other inventors for gene delivery to the brain (Angiopep-2: U.S. Pat. No. 7,557,182; e.g. Ke W, Shao K, Huang R, Han L, Liu Y, Li J, Kuang Y, Ye L, Lou J, Jiang C (2009) Biomaterials 30, 6976-85).

The present invention employs ability of PrP to bind Aβ1-42 and reduce its neurotoxicity combined with drug-delivery properties of functionalized dendrimers. Bi-functional dendrimers carrying BBB-crossing peptide and PrP fragments reactive toward neurotoxic Aβ species are described below. Additionally, the shortest PrP fragments capable of inhibiting neurotoxicity of Aβ peptide, useful for the synthesis of the conjugates, are disclosed. Thus, the aim of the invention, namely development of a drug for use in the treatment of Aβ amyloidogenesis-related pathologies and Aβ-related toxicity, in particular of Alzheimer disease (AD) which employs ability of PrP to bind Aβ1-42 is achieved.

The subject of the present invention are PrP-derived peptides capable of inhibiting neurotoxicity of Aβ and neutralizing toxic species of Aβ for the treatment of Alzheimer disease (AD); wherein the PrP-derived peptides in particular encompass sequences of the N1 fragment:

```
                                           SEQ ID NO: 1
PrP amino acid residues 23-50 (PrP23-50),
KKRPKPGGWNTGGSRYPGQGSPGGNRYP
and
                                           SEQ ID NO: 2
PrP amino acid residues 90-112 (PrP90-112),
GQGGGTHSQWNKPSKPKTNMKHM.
```

The next subject of the present invention are PrP-derived peptides capable of inhibiting neurotoxicity of Aβ and neutralizing toxic species of Aβ for use in the treatment of Alzheimer disease (AD); wherein the PrP-derived peptides in particular are modified to improve the specificity of their binding to carrier molecules and their efficacy through the addition of a cysteine (C) residue, and encompass modified sequences of the N1 fragment:

```
                                           SEQ ID NO: 3
PrP amino acid residues 23-50 with introduced
C-terminal cysteine (PrP23-50-C),
KKRPKPGGWNTGGSRYPGQGSPGGNRYPC
and
                                           SEQ ID NO: 4
PrP amino acid residues 90-112 with introduced N-
terminal cysteine (C-PrP90-112),
CGQGGGTHSQWNKPSKPKTNMKHM.
```

The next subject of the present invention is a conjugate for the treatment of AD, encompassing a carrier molecule and one or more peptides selected from the peptides with SEQ ID NO: 1 or SEQ ID NO: 3, and/or one or more peptides selected from the peptides with SEQ ID NO: 2 or SEQ ID NO: 4, which are produced by known means capable of producing peptides of a purity sufficient for medical use, preferably through direct chemical synthesis, and the treatment is used in human, wherein the carrier molecule creates a functional analogue of the complete N1 molecule from the N-terminus-proximate and C-terminus-proximate peptide sequences without the known drawbacks of the complete N1 sequence, and wherein the carrier molecule is preferably a pharmacologically admissible molecule, and wherein preferably it is a low-generation dendrimer, most preferably PAMAM.

The next subject of the present invention is a conjugate for the treatment of AD as described above, wherein the carrier and peptide are interspaced with a linker molecule, wherein preferably the linker molecule is a pharmacologically admissible molecule, and wherein the linker is preferably PEG.

The next subject of the present invention is a conjugate for the treatment of AD as described above, which further contains a means of substantially increasing its penetration of the brain blood barrier (BBB), wherein said means preferably constitutes a peptide, wherein said peptide preferably is an LRP ligand such as Angiopep, lactoferrin or transferrin or a functional analogue thereof, preferably Angiopep.

The next subject of the present invention is a conjugate for the treatment of AD as described above, wherein at least one amino acid in the peptide sequences SEQ ID NO: 1, SEQ ID NO: 3, SEQ ID NO: 2 and/or SEQ ID NO: 4 is D-amino-acid, preferably more than one amino acid is D-amino-acid, more preferably all amino acids in the peptide sequences SEQ ID NO: 1, SEQ ID NO: 3, SEQ ID NO: 2 and/or SEQ ID NO: 4 are D-amino-acids, in order to decrease rate of degradation of the peptide.

The next subject of the present invention is a method of producing a conjugate for the treatment of AD, encompassing a carrier molecule and one or more copies of peptides SEQ ID NO: 1 or SEQ ID NO: 3, and/or one or more copies of peptides SEQ ID NO: 2 or SEQ ID NO: 4, wherein the carrier molecule creates a functional analogue of the complete N1 molecule from the N-terminus-proximate and C-terminus-proximate peptide sequences without the known drawbacks of the complete N1 sequence, and wherein the carrier molecule is preferably a pharmacologically admissible molecule, and wherein preferably it is a low-generation dendrimer, most preferably PAMAM, which comprises formation of covalent bonds between modified surface groups of dendrimer and reactive groups of peptides selected from PrP-derived peptides and/or BBB-penetrating peptide, preferably LRP ligand such as Angiopep, lactoferrin or transferrin or a functional analogue thereof.

The next subject of the present invention is a method of producing a conjugate for the treatment of AD, encompassing a carrier molecule and one or more copies of peptides SEQ ID NO: 1 or SEQ ID NO: 3, and/or one or more copies of peptides SEQ ID NO: 2 or SEQ ID NO: 4, wherein the carrier molecule creates a functional analogue of the complete N1 molecule from the N-terminus-proximate and C-terminus-proximate peptide sequences without the known drawbacks of the complete N1 sequence, and wherein the carrier molecule is preferably a pharmacologically admissible molecule, and wherein preferably it is a low-generation dendrimer, most preferably PAMAM, wherein the carrier and peptide are interspaced with a linker molecule, wherein preferably the linker molecule is a pharmacologically-admissible molecule, and wherein the linker is preferably PEG, which comprises formation of covalent bonds between unmodified surface groups of the dendrimer and respective groups of bi-functional PEG linker and subsequently formation of the covalent bonds between obtained dendrimer with covalently attached linker molecules and reactive groups of peptides selected from PrP-derived peptides and/or BBB-penetrating peptide, preferably LRP ligand such as Angiopep, lactoferrin or transferrin or a functional analogue thereof via the bi-functional PEG linker.

The next subject of the present invention is the use of a composition encompassing a carrier molecule and one or more copies of peptides SEQ ID NO: 1 or SEQ ID NO: 3, and/or one or more copies of peptides SEQ ID NO: 2 or SEQ ID NO: 4, wherein the carrier molecule creates a functional analogue of the complete N1 molecule from the N-terminus-proximate and C-terminus-proximate peptide sequences without the known drawbacks of the complete N1 sequence, and wherein the carrier molecule is preferably a pharmacologically admissible molecule, and wherein preferably it is a low-generation dendrimer, most preferably PAMAM, wherein the carrier and peptide may be interspaced with a linker molecule, wherein preferably the linker molecule is a pharmacologically admissible molecule, and wherein the linker is preferably PEG, wherein the conjugate further may contain a means of substantially increasing its penetration of the brain-blood barrier (BBB), wherein said means preferably constitutes a peptide, wherein said peptide preferably is an LRP ligand such as Angiopep, lactoferrin or transferrin or a functional analogue thereof, preferably Angiopep, in the treatment of Aβ amyloidogenesis-related pathology and Aβ-related toxicity, in particular of Alzheimer disease (AD).

One embodiment of the present invention comprises the shortest PrP fragments capable of inhibiting the neurotoxicity of the Aβ peptide. These fragments are human PrP sequences SEQ ID NO: 1 and SEQ ID NO: 2.

To assure specific coupling of the peptides to a carrier or a linker, an additional cysteine residue may be introduced at the C-terminus of PrP23-50 and at the N-terminus of PrP90-112, forming SEQ ID NO: 3 and SEQ ID NO: 4. The synthesis of peptides composed of D-amino acid residues may be used to further increase their proteolytic stability in the organism. The peptides may be synthesized by any known means yielding a sufficiently pure peptide, such as direct chemical synthesis or synthesis in a biological system, with further processing and purification, preferably through direct chemical synthesis in a medically certified facility.

The potential therapeutic activity of the peptides can be assessed by standard assays known from the state of the art to the skilled person. Exemplary assays are mentioned below. Effects of the peptides on the rate of amyloidogenesis of Aβ can be monitored by the measurements of the fluorescence emitted by amyloid-bound Thioflavin T (ThT), whereas influence of the peptides on the neurotoxicity of Aβ can be assessed in neuronal cell culture by the measurements of lactate dehydrogenase (LDH) released by dead cells (as described in the captions for FIGS. 3 and 4). Furthermore, the peptides can be analyzed for influence on Aβ-induced impairment of LTP in hippocampal slices.

For clarity, the description of the present invention is supplemented with the following Figures.

FIGURES

FIG. 1. Schematic representation of crucial reactions upon synthesis of the exemplary conjugates of PAMAM, PEG and peptides. Formation of amide and thioeter bond is shown in (A) and (B), respectively. Molecules shown are not to scale.

Figure 2:
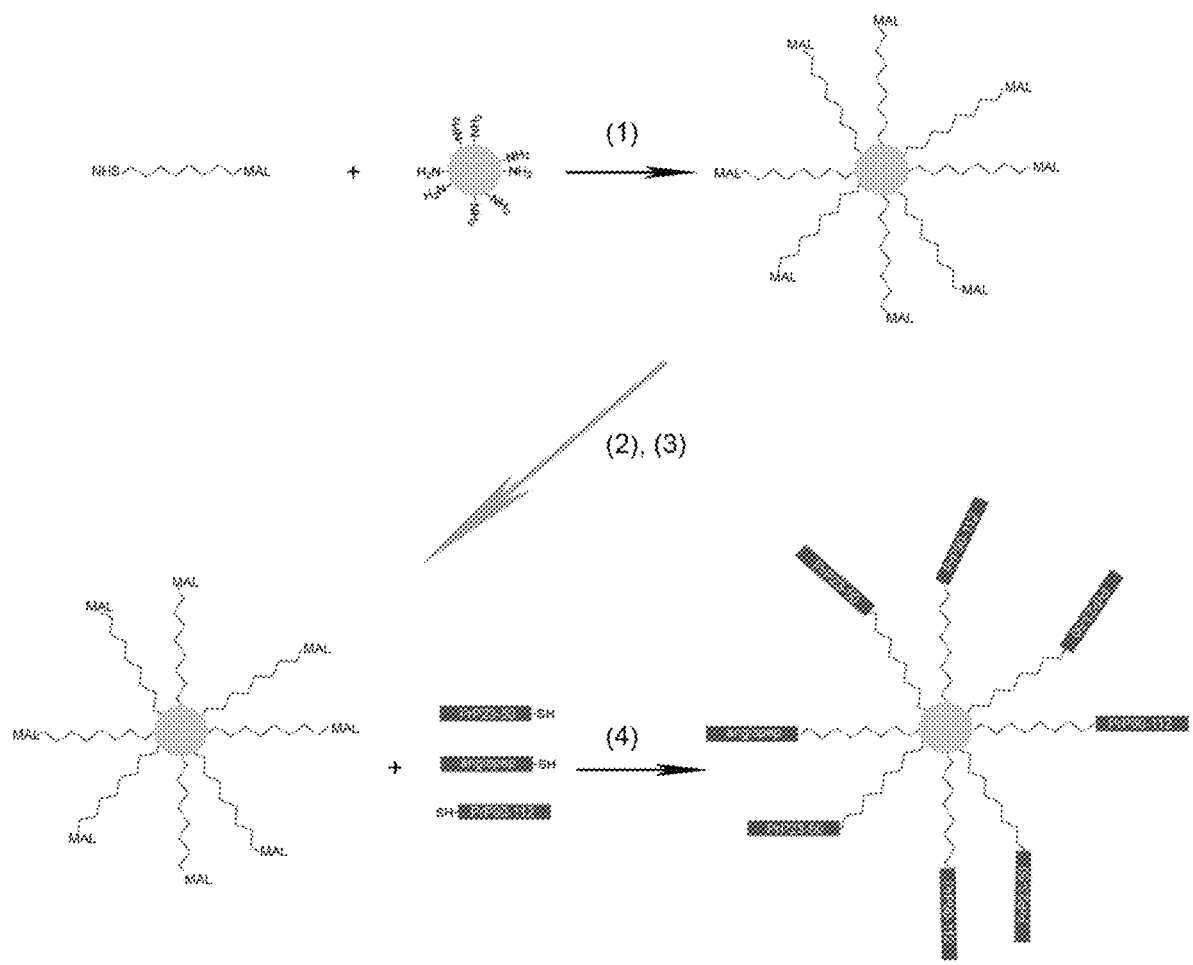

FIG. 2. Schematic representation of crucial stages of synthesis of the exemplary conjugates of PAMAM, PEG and peptides. The stages of the procedure described above are indicated by numbers in brackets. Molecules shown are not to scale.

Figure 3:
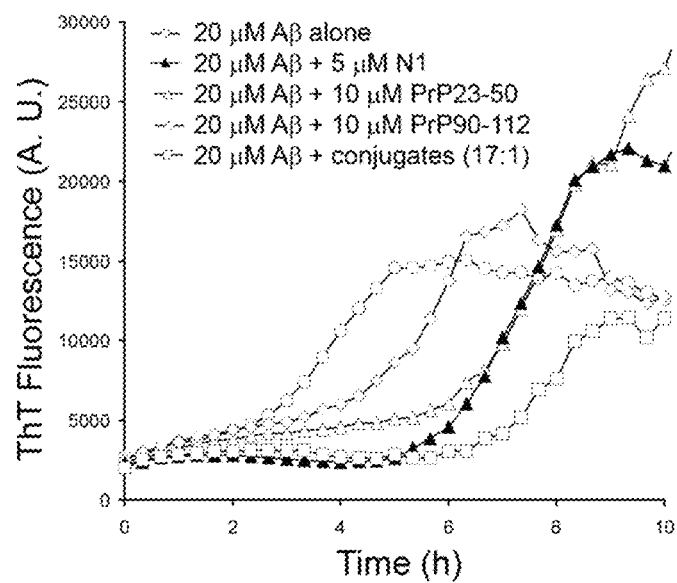

FIG. 3. Effect of the exemplary conjugates on the rate of amyloidogenesis of Aβ1-42 as monitored by ThT fluorescence. Raise in the fluorescence corresponds to the increase in the concentration of amyloid fibrils of Aβ. Curves representing amyloidogenesis of 20 μM Aβ1-42 alone and Aβ1-42 in the presence of unconjugated PrP fragments (concentrations indicated in the Figure) are also shown. The conjugates were used diluted 17 times (indicated as 17:1). Note that the used conjugates of PAMAM(G1)-PEG with peptides PrP23-50 and PrP90-112 retain ability to inhibit amyloidogenesis of Aβ similarly to unmodified PrP23-110 fragment (N1). Effect of the uncoupled short peptides (PrP23-50 and PrP90-112) was apparent but weaker than that of N1.

Figure 4:
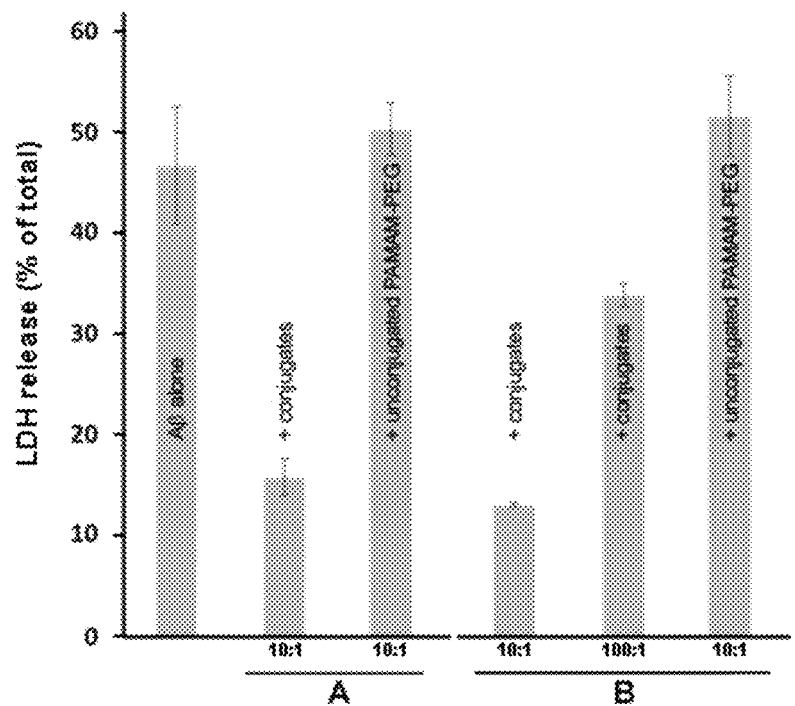

FIG. 4. Effect of the exemplary conjugates on the neurotoxicity of Aβ1-42 assessed by the release of lactate dehydrogenase (LDH) by hippocampal neurons. In this assay, concentration of the LDH released to the cell culture medium corresponds to the number of dead cells and reflects cytotoxicity of Aβ. The measurements of released LDH by the neuronal culture treated with 0.5 μM Aβ1-42 alone and Aβ1-42 in the presence of unconjugated PAMAM(G1)-PEG dendrimers are also shown. In (A) the culture has been treated with Aβ1-42 assembles formed in the presence of dendrimers or conjugates. In (B) the culture has been treated with mixtures of dendrimers or conjugates with Aβ1-42 oligomers preformed in the absence of these additives. The conjugates were used diluted 10 or 100 times (indicated as 10:1 and 100:1). Note that the used conjugates of PAMAM (G1)-PEG with peptides PrP23-50 and PrP90-112 efficiently suppress cytotoxicity of Aβ by inhibiting formation of toxic species of Aβ (A), as well as by neutralizing preformed toxic species of Aβ (B). At the same time, unconjugated PAMAM (G1)-PEG dendrimers have no effect on the toxicity of Aβ.

To facilitate a better understanding of the present invention, the description of the present invention includes the following, non-limiting examples. It will be evident to those skilled in the art that a great number of developments of the present solution are possible, which nevertheless fall within the scope of the present invention.

EXAMPLES

Example 1

In order to mimic the flexible N-terminal part of the PrP molecule, the peptides may be conjugated to a dendrimer, thus present invention relates to conjugates formed between PrP fragments (neutralizing toxic Aβ species) and a dendrimer. In addition to the PrP fragments, the dendrimer is preferably additionally conjugated with a BBB-penetrating peptide.

The conjugates according to the invention have the general formula:

$$D\text{-}(L)_N\text{-}(R_{PrP}+R_{BBBpp})_N$$

wherein
D is the dendrimer;
L is the linker;
R are the peptides: $R_{PrP}$—fragments of PrP and $R_{BBBpp}$—BBB-penetrating peptide eg. LRP ligand;
N is the number of the dendrimer surface (reactive) groups capable of forming covalent bonds with L.

The conjugates of the invention can be based on different types of dendrimers (D), often commercially available, like polyamidoamine (PAMAM) dendrimers, polypropylenimine (PPI) dendrimers or phosphorus dendrimers; and of various generations. Since yield of the cross-linking is relatively low and therefore high concentrations of PrP fragments must be used, employment of low-generation dendrimers is optimal to ensure that all reactive groups (of dendrimer) will be modified upon the reaction.

Linker (L) is selected from the group of bi-functional PEG cross-linkers of broad range of lengths (n, number of ethylene glycol units).

The peptides (R) conjugated to the dendrimers (D) are selected from the group consisting of: ($R_{PrP}$) human PrP fragments retaining ability to neutralize toxic Aβ peptide, such as PrP23-112, PrP23-50 and PrP90-112, or other fragments encompassing these sequences;

($R_{BBBpp}$) BBB-penetrating human peptide belonging to the ligands of LRP, such as Angiopep, lactoferrin or transferrin. In the conjugate, the molar ratio of PrP peptides to BBB-penetrating peptide is higher than 2.

The schematic representations of crucial reactions (amide and thioether bond formations) and stages of the synthesis of the exemplary conjugates are shown in FIG. 1 and FIG. 2, respectively.

Such exemplary conjugates can be synthesized as follows:
(1) in the first step, primary amino groups of PAMAM dendrimers (0.5 mM, commercially available Dendritech PAMAM dendrimers of $1^{st}$ generation (G1), carrying 8 primary amino groups, MW=1429 Da) react with succinimide (NHS) groups of the hetero-bi-functional PEG (commercially available Sigma-Aldrich NHS-PEG-MAL, 27 ethylene glycol units, MW=1570 Da) in the buffer composed of PBS pH 7.4 and 0.5 mM EDTA (the molar ratio of PAMAM to NHS-PEG-MAL is 1:16);

(2) the reaction with NHS group is attenuated by incubation with 12.5 mM glycine in 100 mM Tris-HCl pH 7.4;

(3) unreacted substrates (dendrimers and NHS-PEG-MAL) are removed by ultrafiltration using centrifugal filter units of molecular weight cut-off (MWCO) 10 kDa (commercially available Microcon filter units with regenerated cellulose membrane) and simultaneously the buffer is exchanged for PBS;

(4) in the next step, maleimide (MAL) groups of PAMAM-PEG-MAL react with thiol groups of cysteine residues of PrP peptides and Angiopep (the molar ratio of PAMAM-PEG-MAL to PrP23-50 is about 1:8 and the molar ratio of PrP23-50 to PrP90-112 to Angiopep is 4:3:1);

(5) unreacted substrates (PAMAM-PEG-MAL and the peptides) are removed by filtration using centrifugal filter units of MWCO 30 kDa and the buffer is exchanged for PBS. Cross-linking products can be analyzed by SDS-PAGE and Western blotting with appropriate antibodies.

Example 2

In another embodiment, the present invention also relates to the conjugates formed without a PEG linker, of the general formula:

$$D\text{-}(R_{PrP}+R_{BBBpp})_N$$

wherein

D is the dendrimer;

R are the peptides: fragments of PrP ($R_{PrP}$) and LRP ligands-BBB-penetrating peptide ($R_{BBBpp}$);

N is the number of the dendrimer surface (reactive) groups capable of forming covalent bonds directly with R.

Such exemplary conjugates can be synthesized as follows: (1) in the first step, primary amino groups of PAMAM dendrimers of $1^{st}$ generation are modified by reacting with succinimide groups of NHS-MAL crosslinker (e.g. N-α-maleimidoacet-oxysuccinimide ester or other amine-to-sulfhydryl crosslinker) in the buffer composed of PBS pH 7.4 and 0.5 mM EDTA (the molar ratio of PAMAM to NHS-MAL is 1:16);

(2) the reaction with NHS group is attenuated by incubation with 100 mM glycine in 12.5 mM Tris-HCl pH 7.4;

(3) unreacted substrates (dendrimers and NHS-MAL) are removed by ultrafiltration using centrifugal filter units of molecular weight cut-off (MWCO) 2 kDa (filter units with regenerated cellulose membrane) and simultaneously the buffer is exchanged for PBS;

(4) in the next step, maleimide groups of PAMAM-MAL react with thiol groups of cysteine residues of PrP peptides and Angiopep (the molar ratio of PAMAM-MAL to PrP23-50 is about 1:8 and the molar ratio of PrP23-50 to PrP90-112 to Angiopep is 4:3:1);

(5) unreacted substrates (PAMAM-MAL and the peptides) are removed by filtration using centrifugal filter units of MWCO 20 kDa and the buffer is exchanged for PBS. Cross-linking products can be analyzed by SDS-PAGE and Western blotting with appropriate antibodies.

Example 3

Potential therapeutic activity of the conjugates can be assessed by standard assays. Exemplary assays are listed below. Effects of the conjugates on the rate of amyloidogenesis of Aβ can be monitored by the measurements of the fluorescence emitted by amyloid-bound ThT (FIG. 3). Raise in the fluorescence corresponds to the increase in the concentration of amyloid fibrils of Aβ. Curves representing amyloidogenesis of 20 μM Aβ1-42 alone and Aβ1-42 in the presence of unconjugated PrP fragments (concentrations indicated in the Figure) are also shown. The conjugates were used diluted 17 times (indicated as 17:1). Note that the used conjugates of PAMAM(G1)-PEG with peptides PrP23-50 and PrP90-112 retain ability to inhibit amyloidogenesis of Aβ similarly to unmodified PrP23-110 fragment (N1). Effect of the uncoupled short peptides (PrP23-50 and PrP90-112) was apparent but weaker than that of N1.

Influence of the conjugates on the neurotoxicity of Aβ can be assessed in neuronal cell culture by the measurements of LDH released by dead cells (FIG. 4). In this assay, concentration of the LDH released to the cell culture medium corresponds to the number of dead cells and reflects cytotoxicity of Aβ. The measurements of released LDH by the neuronal culture treated with 0.5 μM Aβ1-42 alone and Aβ1-42 in the presence of unconjugated PAMAM(G1)-PEG dendrimers are also shown. In (A) the culture has been treated with Aβ1-42 assembles formed in the presence of dendrimers or conjugates. In (B) the culture has been treated with mixtures of dendrimers or conjugates with Aβ1-42 oligomers preformed in the absence of these additives. The conjugates were used diluted 10 or 100 times (indicated as 10:1 and 100:1). Note that the used conjugates of PAMAM (G1)-PEG with peptides PrP23-50 and PrP90-112 efficiently suppress cytotoxicity of Aβ by inhibiting formation of toxic species of Aβ (A), as well as by neutralizing preformed toxic species of Aβ (B). At the same time, unconjugated PAMAM (G1)-PEG dendrimers have no effect on the toxicity of Aβ. In order to analyze effects on the formation of toxic Aβ species, the conjugates are incubated with monomeric (freshly prepared) Aβ, whereas to demonstrate neutralizing activity, the conjugates are incubated with preformed toxic assemblies of Aβ.

The exemplary conjugates of PAMAM with peptides PrP23-50 and PrP90-112 retain ability to inhibit amyloidogenesis of Aβ1-42 peptide similarly to unmodified N-terminal fragment of PrP-N1 (PrP23-110), as demonstrated in FIG. 3. Importantly, these conjugates efficiently suppress cytotoxicity of Aβ1-42 oligomers in the primary culture of rat hippocampal neurons (FIG. 4). Furthermore, the conjugates are capable of inhibiting formation of neurotoxic species of Aβ as well as neutralizing preformed neurotoxic oligomers of Aβ (FIG. 4). At the same time, unconjugated PAMAM dendrimers have no effect on amyloidogenesis (data not shown) and neurotoxicity of Aβ (FIG. 4).

The conjugates can be also analyzed for influence on Aβ-induced impairment of LTP in hippocampal slices, as described for PrP in (Scott-McKean J J, Surewicz K, Choi J K, Ruffin V A, Salameh A I, Nieznanski K, Costa A C, Surewicz W K (2016) *Neurobiol. Dis.* 91, 124-31). Furthermore, activity of the conjugates can be analyzed in animal models of AD. Importantly, the conjugates can be applied by intravenous injections. Animals can be subjected to standard behavioural tests assessing impairment of learning and memory, and subsequently, their brains analyzed by histopathological methods for deposition of Aβ plaques and loss of neurons.

The studies were supported by grant 2013/10/M/NZ4/00311 from the Polish National Science Centre.

The invention claimed is:

1. A PrP-derived peptide fragment mutant having the amino acid sequence set forth in SEQ ID NO: 3.

2. A conjugate comprising (i) one or more PrP-derived peptide fragments having the amino acid sequences set forth in i-SEQ ID NO: 1 and SEQ ID NO: 3 and one or more additional PrP-derived peptide fragments having the amino acid sequences set forth in SEQ ID NO: 2 and SEQ ID NO: 4 and (ii) a dendrimer.

3. The A-conjugate according to claim 2, characterised in that the dendrimer carrier and peptide are connected via a linker molecule.

4. The conjugate of claim 3, wherein the linker molecule is polyethylene glycol (PEG).

5. The conjugate according to claim 2, characterised in that it further contains a blood-brain barrier (BBB)-penetrating peptide.

6. The conjugate of claim 5, wherein the BBB-penetrating peptide is a low density lipoprotein receptor-related protein (LRP) ligand selected from the group consisting of Angiopep, lactoferrin or transferrin, or a functional analogue thereof.

7. The conjugate according to claim 2, characterised in that at least one amino acid in at least one of sequences SEQ ID NO: 1, SEQ ID NO: 3, SEQ ID NO: 2 and SEQ ID NO: 4 is a D-amino acid.

8. A method of treating Aβ amyloidogenesis-related pathology and/or Aβ-related toxicity in a subject, said method comprising administering to a subject in need thereof a therapeutically effective amount of the conjugate of claim 2, thereby treating an Aβ amyloidogenesis-related pathology and/or Aβ-related toxicity.

9. The method of claim 8, wherein the AP amyloidogenesis-related pathology is Alzheimer's disease.

10. A method of treating a familial/heritable form of Alzheimer disease (fAD) in a subject, said method comprising administering to a subject in need thereof a therapeutically effective amount of the conjugate of claim 2, thereby treating fAD, wherein overproduction and/or accumulation of AP is observed in the subject, and wherein the overproduction and/or accumulation of AP is a result of genetic mutations in the subject.

11. A method of manufacturing the conjugate of claim 2, comprising forming covalent bonds between modified surface groups of a dendrimer and reactive groups of peptides, wherein the peptides are selected from PrP-derived peptides according to one or more of SEQ ID NO: 1, SEQ ID NO: 3, SEQ ID NO: 2 and SEQ ID NO: 4 and/or a BBB-penetrating peptide.

12. The method of claim 11, wherein the BBB-penetrating peptide is an LRP ligand selected from the group consisting of Angiopep, lactoferrin or transferrin, or a functional analogue thereof.

13. The method according to claim 11, wherein thiol groups (—SH) are the reactive groups.

14. A method of manufacturing the conjugate of claim 2, comprising
  (a) forming covalent bonds between unmodified surface groups of a dendrimer and respective groups of a bi-functional PEG linker, and
  (b) forming covalent bonds between the PEG linker of (a) and reactive groups of peptides, wherein the peptides are selected from PrP-derived peptides according to one or more of SEQ ID NO: 1, SEQ ID NO: 3, SEQ ID NO: 2 and SEQ ID NO: 4 and/or a BBB-penetrating peptide.

15. The method according to claim 14, wherein thiol groups (—SH) are the reactive groups.

16. The method of claim 14, wherein the BBB-penetrating peptide is an LRP ligand selected from the group consisting of Angiopep, lactoferrin or transferrin, or a functional analogue thereof.

17. The conjugate of claim 2, wherein the dendrimer is a low-generation dendrimer.

18. The conjugate of claim 2, wherein the dendrimer is a polyamidoamine (PAMAM) dendrimer.

* * * * *

SEQUENCE LISTING

```
<160> NUMBER OF SEQ ID NOS: 4

<210> SEQ ID NO 1
<211> LENGTH: 28
<212> TYPE: PRT
<213> ORGANISM: Homo sapiens
<220> FEATURE:
<221> NAME/KEY: MISC_FEATURE
<223> OTHER INFORMATION: PrP amino acid residues 23-50 (PrP23-50)

<400> SEQUENCE: 1

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro
            20                  25

<210> SEQ ID NO 2
<211> LENGTH: 23
<212> TYPE: PRT
<213> ORGANISM: Homo sapiens
<220> FEATURE:
<221> NAME/KEY: MISC_FEATURE
<223> OTHER INFORMATION: PrP amino acid residues 90-112 (PrP90-112)

<400> SEQUENCE: 2

Gly Gln Gly Gly Gly Thr His Ser Gln Trp Asn Lys Pro Ser Lys Pro
1               5                   10                  15

Lys Thr Asn Met Lys His Met
            20

<210> SEQ ID NO 3
<211> LENGTH: 29
<212> TYPE: PRT
<213> ORGANISM: Artificial Sequence
<220> FEATURE:
<223> OTHER INFORMATION: PrP amino acid residues 23-50 with introduced
      C-terminal cysteine (PrP23-50-C)

<400> SEQUENCE: 3

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Cys
            20                  25

<210> SEQ ID NO 4
<211> LENGTH: 24
<212> TYPE: PRT
<213> ORGANISM: Artificial Sequence
<220> FEATURE:
<223> OTHER INFORMATION: PrP amino acid residues 90-112 with introduced
      N-terminal cysteine (C-PrP90-112)

<400> SEQUENCE: 4

Cys Gly Gln Gly Gly Gly Thr His Ser Gln Trp Asn Lys Pro Ser Lys
1               5                   10                  15

Pro Lys Thr Asn Met Lys His Met
            20
```